United States Patent [19]

Kane et al.

[11] Patent Number: 5,587,310

[45] Date of Patent: Dec. 24, 1996

[54] CHIMERIC BLOOD COAGULATION PROTEINS

[75] Inventors: William H. Kane; Thomas L. Ortel, both of Durham, N.C.

[73] Assignee: Duke University, Durham, N.C.

[21] Appl. No.: 273,362

[22] Filed: Jul. 11, 1994

Related U.S. Application Data

[63] Continuation of Ser. No. 975,839, Nov. 13, 1992, abandoned.

[51] Int. Cl.$^6$ .................... C07K 14/745; C07K 14/755; C12N 5/10; C12N 15/12
[52] U.S. Cl. ................ 435/240.2; 435/69.6; 435/254.11; 435/320.1; 530/381; 530/383; 536/23.5
[58] Field of Search .................... 435/69.6, 172.3, 435/240.2, 320.1, 254.11; 530/381, 383; 930/100; 536/23.5

[56] References Cited

U.S. PATENT DOCUMENTS

| | | | |
|---|---|---|---|
| 4,849,407 | 7/1989 | Murray et al. | 514/12 |
| 5,004,803 | 4/1991 | Kaufman et al. | 530/383 |

OTHER PUBLICATIONS

D. Scandella et al., 74 *Blood* 1618 (1989).
D. Scandella et al., 67 *Thromb. Haemost.* 665 (1992).
J. Toole et al., 312 *Nature* 342 (1984).
G. Vehar et al., 312 *Nature* 337 (1984).
L. D. Cripe, et al., *Biochemistry* 31, 3777–3785 (1992).
W. H. Kane et al.; *Blood* 71, 539–555 (1988).
W. H. Kane et al., *Biochemistry* 26 6508–6514 (1987).
W. H. Kane et al., *Proc. Natl. Acad. Sci.* 83 6800–6804 (Sep. 1986).
T. L. Ortel et al., *The Journal of Biological Chemistry* 267, 4189–4198 (Feb. 1992).
Chiu et al. (1985) Blood 65, 810–818.

*Primary Examiner*—Dian C. Jacobson
*Attorney, Agent, or Firm*—Bell, Seltzer, Park & Gibson

[57] ABSTRACT

Chimeric blood coagulation proteins are disclosed. The proteins are (i) coagulation factor V in which at least one A3, C1 or C2 domain exon thereof is replaced with the homologous exon of coagulation factor VIII; or (ii) coagulation factor VIII in which at least one A3, C1 or C2 domain exon thereof is replaced with the homologous exon of coagulation factor V. The chimeric proteins are useful for diagnostic purposes in epitope mapping and for therapeutic purposes in facilitating blood coagulations in patients in need of such treatment.

15 Claims, 1 Drawing Sheet

CHIMERIC BLOOD COAGULATION PROTEINS

This invention was made with Government Support under Grant Number RO1 HL43106 from the National Institutes of Health. The Government has certain rights to this invention.

This is a continuation of application Ser. No. 07/975,839 filed on 13 Nov. 1992, now abandoned.

FIELD OF THE INVENTION

This invention relates to blood coagulation proteins, and particularly relates to Factor VIII and Factor V.

BACKGROUND OF THE INVENTION

Approximately 10–20% of hemophiliacs who receive multiple factor VIII treatments develop alloantibodies that inactivate factor VIII. The development of such factor VIII inhibitors is a serious complication which can result in major bleeding episodes that are difficult to treat. Current therapies include high dose human or porcine factor VIII, steroids, intravenous immune globulin, plasmapheresis, and recombinant factor VIIa. Similar problems may occur in patients undergoing treatment for factor V deficiency. Despite these interventions, many patients require large amounts of blood products during bleeding episodes. Accordingly, there is a continued need for new ways of diagnosing and combating the development of inhibitory alloantibodies in patients undergoing treatment with blood coagulation proteins.

D. Scandella et al., *Blood* 74, 1618 (1989), describe an *E. coli* expression system for the epitope mapping of factor VIII inhibitors.

D. Scandella et al., *Thromb. Haemost.* 67, 665 (1992) describe a baculovirus expression system for epitope mapping of factor VIII with recombinant factor VIII peptides.

U.S. Pat. No. 5,004,803 to R. Kaufman and D. Pittman describe recombinant DNA coding for factor VIII in which its B domain is replaced with the B domain peptide sequence of factor V. This reference is concerned with obviating problems in the secretion of factor VIII, and not with the active forms of the blood coagulation protein. Note that the sequences of human factor V and VIII are about 40% identical except in the B domain, where there is little homology. See, e.g., J. Toole et al. *Nature* 312, 342 (1984); G. Vehar et al., *Nature* 312, 337 (1984).

SUMMARY OF THE INVENTION

Chimeric blood coagulation proteins are disclosed herein. The chimeric proteins are selected from the group consisting of:

coagulation factor V in which at least one A3, C1 or C2 domain exon thereof is replaced with the homologous exon of coagulation factor VIII; and coagulation factor VIII in which at least one A3, C1 or C2 domain exon thereof is replaced with the homologous exon of coagulation factor V.

Chimeric proteins of the instant invention are useful for diagnostic purposes to epitope map alloantibody inhibitors in a patient undergoing treatment with a blood coagulation protein to facilitate the design and implementation of a specific therapy based on the inhibitor specificity.

Chimeric proteins of the present invention are also useful as therapeutic agents in patients with inhibitors which interact with the replaced epitopes of the chimeric blood coagulation protein.

The foregoing and other objects and aspects of the present invention are explained in detail in the drawings herein and the specification set forth below.

BRIEF DESCRIPTION OF THE DRAWINGS

The Figure provides a comparison of the domain structures and exon-intron structures for the factor V and factor VIII proteins. The boxes represent the domain structures for factor V and factor VIII. The identities of the A1, A2, B, A3, C1, and C2 domains are indicated by the letters. The arrows indicate the location of introns which are removed from the mature mRNA. The number of each intron in the gene for factor V or factor VIII is indicated. Exons 1-25 of the Factor V protein and exons 1-26 of the factor VIII protein are defined by the regions between the arrows, with exons occuring sequentially from left to right.

DETAILED DESCRIPTION OF THE INVENTION

Figure 1:
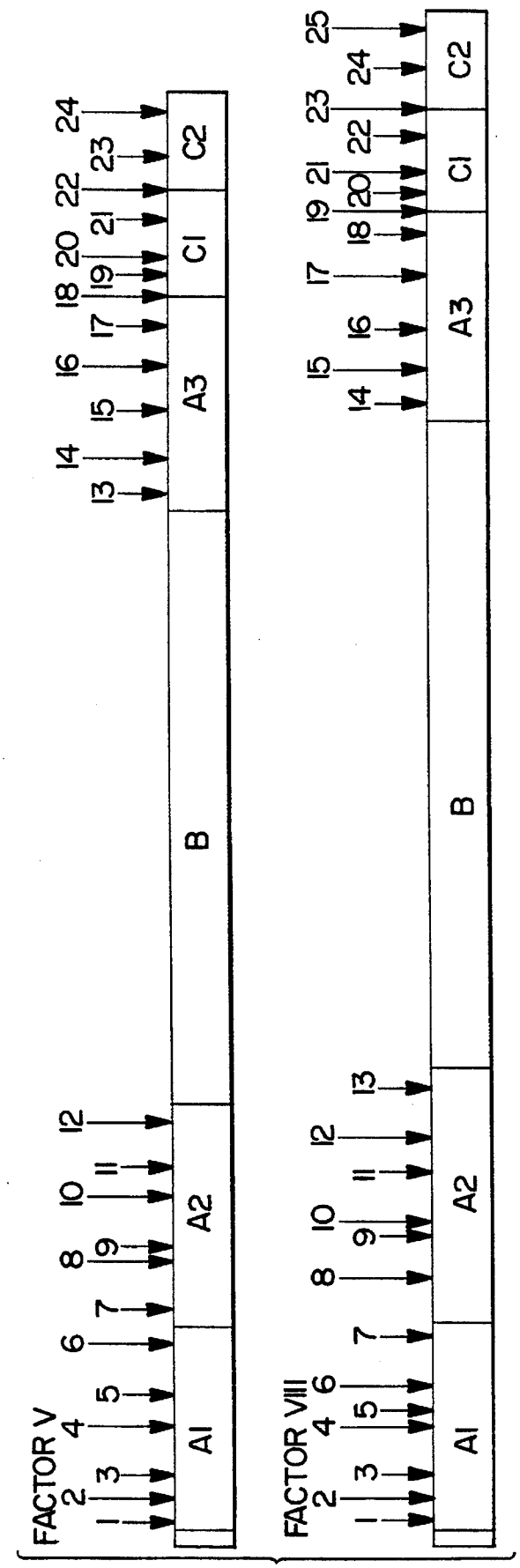

Amino acid sequences disclosed herein are presented in the amino to carboxy direction, from left to right. The amino and carboxy groups are not presented in the sequence. Nucleotide sequences are presented herein by single strand only, in the 5' to 3' direction, from left to right.

As noted above, the Figure (adapted from L. Cripe et al., *Biochem.* 31, 3777 (1992)), provides a comparison of the domain structures and exon-intron structures for the factor V and factor VIII proteins. The boxes represent the domain structures for factor V and factor VIII. The identities of the A1, A2, B, A3, C1, and C2 domains are indicated by the letters and correspond to the amino acid sequences described in W. Kane and E. Davie, *Blood* 71, 539 (1988). The DNA sequences for human factor VIII and human factor V, the locations of introns and exons, and the sequences of the intron-exon junctions, are known. See, e.g., L. Cripe et al., *Biochem.* 31, 3777 (1992). The arrows in the Figure indicate the location of introns which are removed from the mature mRNA. The number of each intron in the gene for factor V or factor VIII is indicated. Exons 1-25 of the Factor V protein and exons 1-26 of the factor VIII protein are defined by the regions between the arrows, with exons occuring sequentially from left to right (5' to 3'). Those skilled in the art will appreciate that, while the term "exon" is ordinarily used to refer to a region of a genomic DNA which is expressed, the term "exon" is used herein to refer to the portion of the protein encoded by that DNA region.

A single exon or a plurality of exons may be exchanged in the chimera, as illustrated in greater detail below. Where a plurality of exons are exchanged, they may be separate by one or more intervening exons which are not exchanged or, more typically, are adjacent. Where the exchanged exons are adjacent, the number of exons exchanged may be, for example from about 1 to 5 exons, but will more typically be from 2 to 3. As noted above, in many embodiments, a single exon is exchanged.

Some specific examples of chimeric blood coagulation proteins of the present invention are set forth below. Note that factor VIII exons 5 and 6 are sometimes treated as a single exon herein because the two together correspond to exon 5 alone of factor V (due to an additional intron found in factor VIII). Note also that, while the chimeric proteins of the present invention are herein described with reference to human blood coagulation proteins, those skilled in the art will appreciate that the invention may be embodied in other mammalian factor V and factor VIII proteins, including the bovine, porcine, and ovine homologs thereof, with variations in intron structure being treated in like manner to the variation in intron structure between human factor V and factor VIII.

Factor $VIII_{(VIII\text{-}15;V\text{-}14)}$;
Factor $VIII_{(VIII\text{-}16;V\text{-}15)}$;
Factor $VIII_{(VIII\text{-}17;V\text{-}16)}$;
Factor $VIII_{(VIII\text{-}18;V\text{-}17)}$;
Factor $VIII_{(VIII\text{-}19;V\text{-}18)}$;
Factor $VIII_{(VIII\text{-}20;V\text{-}19)}$;
Factor $VIII_{(VIII\text{-}21;V\text{-}20)}$;
Factor $VIII_{(VIII\text{-}22;V\text{-}21)}$;
Factor $VIII_{(VIII\text{-}23;V\text{-}22)}$;
Factor $VIII_{(VIII\text{-}24;V\text{-}23)}$;
Factor $VIII_{(VIII\text{-}25;V\text{-}24)}$;
Factor $VIII_{(VIII\text{-}26;V\text{-}25)}$;
Factor $V_{(V\text{-}14;VIII\text{-}15)}$;
Factor $V_{(V\text{-}15;VIII\text{-}16)}$;
Factor $V_{(V\text{-}16;VIII\text{-}17)}$;
Factor $V_{(V\text{-}17;VIII\text{-}18)}$;
Factor $V_{(V\text{-}18;VIII\text{-}19)}$;
Factor $V_{(V\text{-}19;VIII\text{-}20)}$;
Factor $V_{(V\text{-}20;VIII\text{-}21)}$;
Factor $V_{(V\text{-}21;VIII\text{-}22)}$;
Factor $V_{(V\text{-}22;VIII\text{-}23)}$;
Factor $V_{(V\text{-}23;VIII\text{-}24)}$;
Factor $V_{(V\text{-}24;VIII\text{-}25)}$; and
Factor $V_{(V\text{-}25;VIII\text{-}26)}$.

In addition, examples of chimeric blood coagulation proteins of the present invention in which two adjacent exons in the A3, C1, or C2 domains are exchanged include:

Factor $VIII_{(VIII\text{-}15;16;V\text{-}14,15)}$;
Factor $VIII_{(VIII\text{-}16,17;V\text{-}15,16)}$;
Factor $VIII_{(VIII\text{-}17,18;V\text{-}16,17)}$;
Factor $V_{(V\text{-}14,15;VIII\text{-}15,16)}$;
Factor $V_{(V\text{-}15,16;VIII\text{-}16,17)}$;
Factor $V_{(V\text{-}16,17;VIII\text{-}17,18)}$;
Factor $VIII_{(VIII\text{-}20,21;V\text{-}19,20)}$;
Factor $VIII_{(VIII\text{-}21,22;V\text{-}20,21)}$;
Factor $VIII_{(VIII\text{-}22,23;V\text{-}21,22)}$;
Factor $VIII_{(VIII\text{-}23,24;V\text{-}22,23)}$;
Factor $VIII_{(VIII\text{-}24,25;V\text{-}23,24)}$;
Factor $VIII_{(VIII\text{-}25,26;V\text{-}24,25)}$;
Factor $V_{(V\text{-}19,20;VIII\text{-}20,21)}$;
Factor $V_{(V\text{-}20,21;VIII\text{-}21,22)}$;
Factor $V_{(V\text{-}21,22;VIII\text{-}22,23)}$;
Factor $V_{(V\text{-}22,23;VIII\text{-}23,24)}$;
Factor $V_{(V\text{-}23,24;VIII\text{-}24,25)}$; and
Factor $V_{(V\text{-}24,25;VIII\text{-}25,26)}$.

Some examples of chimeras in which three, four, and five adjacent exons are exchanged are the following:

Factor $VIII_{(VIII\text{-}20,21,22;V\text{-}19,20,21)}$;
Factor $VIII_{(VIII\text{-}20,21,22,23;V\text{-}19,20,21,22)}$; and
Factor $VIII_{(VIII\text{-}20,21,22,23,24;V\text{-}19,20,21,22,23)}$.

The foregoing chimeric proteins may be made in accordance with techniques known in the art. The production of recombinant DNA, vectors, host cells, and proteins by genetic engineering techniques is well known. See, e.g., U.S. Pat. No. 4,761,371 to Bell et al. at Col. 6 line 3 to Col. 9 line 65; U.S. Pat. No. 4,877,729 to Clark et al. at Col. 4 line 38 to Col. 7 line 6; U.S. Pat. No. 4,912,038 to Schilling at Col. 3 line 26 to Col. 14 line 12; and U.S. Pat. No. 4,879,224 to Wallner at Col. 6 line 8 to Col. 8 line 59.

DNA sequences encoding chimeric proteins may be recovered by use of the polymerase chain reaction (PCR) procedure and splicing by overlap extension (SOE), as is known in the art. See U.S. Pat. Nos. 4,683,195 to Mullis et al. and 4,683,202 to Mullis.

The chimeric proteins may be synthesized in host cells transformed with vectors containing DNA encoding the chimeric proteins. A vector is a replicable DNA construct. Vectors are used herein either to amplify DNA encoding the chimeric protein and/or to express DNA which encodes the chimeric protein. An expression vector is a replicable DNA construct in which a DNA sequence encoding the chimeric protein is operably linked to suitable control sequences capable of effecting the expression of the chimeric protein in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants.

Vectors useful for practicing the present invention include plasmids, viruses (including phage), retroviruses, and integratable DNA fragments (i.e., fragments integratable into the host genome by homologous recombination). The vector replicates and functions independently of the host genome, or may, in some instances, integrate into the genome itself. Suitable vectors will contain replicon and control sequences which are derived from species compatible with the intended expression host. Transformed host cells are cells which have been transformed or transfected with the chimeric protein vectors constructed using recombinant DNA techniques. Transformed host cells ordinarily express the chimeric protein, but host cells transformed for purposes of cloning or amplifying the chimeric protein DNA need not express the chimeric protein. When expressed, the chimeric protein will typically be located in the host cell membrane.

DNA regions are operably linked when they are functionally related to each other. For example: a promoter is operably linked to a coding sequence if it controls the transcription of the sequence; a ribosome binding site is operably linked to a coding sequence if it is positioned so as to permit translation. Generally, operably linked means contiguous and, in the case of leader sequences, contiguous and in reading phase.

Suitable host cells include prokaryotes, yeast cells or higher eukaryotic cells. Prokaryotes include gram negative or gram positive organisms, for example *Escherichia coli* (*E. coli*) or Bacilli. Higher eukaryotic cells include established cell lines of mammalian origin as described below. Exemplary host cells are *E. coli* W3110 (ATCC 27,325), *E. coli* B, *E. coli* X1776 (ATCC 31,537), and *E. coli* 294 (ATCC 31,446). Pseudomonas species, Bacillus species, and Serratia marcesans are also suitable.

A broad variety of suitable microbial vectors are available. Generally, a microbial vector will contain an origin of replication recognized by the intended host, a promoter which will function in the host and a phenotypic selection gene such as a gene encoding proteins conferring antibiotic resistance or supplying an autotrophic requirement. Similar constructs will be manufactured for other hosts. *E. coli* is typically transformed using pBR322. See Bolivar et al., Gene 2, 95 (1977). pBR322 contains genes for ampicillin and tetracycline resistance and thus provides easy means for identifying transformed cells.

Expression vectors should contain a promoter which is recognized by the host organism. This generally means a promoter obtained from the intended host. Promoters most commonly used in recombinant microbial expression vectors include the beta-lactamase (penicillinase) and lactose promoter systems (Chang et al., *Nature* 275, 615 (1978); and Goeddel et al., *Nature* 281, 544 (1979)), a tryptophan (trp) promoter system (Goeddel et al., *Nucleic Acids Res.* 8, 4057 (1980) and EPO App. Publ. No. 36,776) and the tac promoter (H. De Boer et al., *Proc. Natl. Acad. Sci. USA* 80, 21 (1983)). While these are commonly used, other microbial promoters are suitable. Details concerning nucleotide sequences of many have been published, enabling a skilled worker to operably ligate them to DNA encoding the chimeric protein in plasmid or viral vectors (Siebenlist et al., *Cell* 20, 269 (1980)). The promoter and Shine-Dalgarno sequence (for prokaryotic host expression) are operably linked to the DNA encoding the chimeric protein, i.e., they are positioned so as to promote transcription of the chimeric protein messenger RNA from the DNA.

Eukaryotic microbes such as yeast cultures may be transformed with suitable chimeric protein-encoding vectors. See, e.g., U.S. Pat. No. 4,745,057. *Saccharomyces cerevisiae* is the most commonly used among lower eukaryotic host microorganisms, although a number of other strains are commonly available. Yeast vectors may contain an origin of replication from the 2 micron yeast plasmid or an autonomously replicating sequence (ARS), a promoter, DNA encoding the chimeric protein, sequences for polyadenylation and transcription termination, and a selection gene. An exemplary plasmid is YRp7, (Stinchcomb et al., *Nature* 282, 39 (1979); Kingsman et al., Gene 7, 141 (1979); Tschemper et al., Gene 10, 157 (1980)). This plasmid contains the trp1 gene, which provides a selection marker for a mutant strain of yeast lacking the ability to grow in tryptophan, for example ATCC No. 44076 or PEP4-1 (Jones, *Genetics* 85, 12 (1977)). The presence of the trp1 lesion in the yeast host cell genome then provides an effective environment for detecting transformation by growth in the absence of tryptophan.

Suitable promoting sequences in yeast vectors include the promoters for metallothionein, 3-phosphoglycerate kinase (Hitzeman et al., *J. Biol. Chem.* 255, 2073 (1980) or other glycolytic enzymes (Hess et al., *J. Adv. Enzyme Reg.* 7, 149 (1968); and Holland et al., *Biochemistry* 17, 4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al., EPO Publn. No. 73,657.

Cultures of cells derived from multicellular organisms are a desirable host for recombinant chimeric protein synthesis. In principal, any higher eukaryotic cell culture is workable, whether from vertebrate or invertebrate culture, including insect cells. However, mammalian cells are preferred, as illustrated in the Examples. Propagation of such cells in cell culture has become a routine procedure. See Tissue Culture, Academic Press, Kruse and Patterson, editors (1973). Examples of useful host cell lines are VERO and HeLa cells, Chinese hamster ovary (CHO) cell lines, and WI138, BHK, COS-7, CV, and MDCK cell lines. Expression vectors for such cells ordinarily include (if necessary) an origin of replication, a promoter located upstream from the gene to be expressed, along with a ribosome binding site, RNA splice site (if intron-containing genomic DNA is used), a polyadenylation site, and a transcriptional termination sequence.

The transcriptional and translational control sequences in expression vectors to be used in transforming vertebrate cells are often provided by viral sources. For example, commonly used promoters are derived from polyoma, Adenovirus 2, and Simian Virus 40 (SV40). See, e.g., U.S. Pat. No. 4,599,308. The early and late promoters are useful because both are obtained easily from the virus as a fragment which also contains the SV40 viral origin of replication. See Fiers et al., *Nature* 273, 113 (1978). The vaccinia virus may be used as a vector, as described in the Examples. Further, the chimeric protein promoter, control and/or signal sequences, may also be used, provided such control sequences are compatible with the host cell chosen.

An origin of replication may be provided either by construction of the vector to include an exogenous origin, such as may be derived from SV40 or other viral source (e.g. Polyoma, Adenovirus, VSV, or BPV), or may be provided by the host cell chromosomal replication mechanism. If the vector is integrated into the host cell chromosome, the latter may be sufficient.

Rather than using vectors which contain viral origins of replication, one can transform mammalian cells by the method of cotransformation with a selectable marker and the chimeric protein DNA. An example of a suitable selectable marker is dihydrofolate reductase (DHFR) or thymidine kinase. See U.S. Pat. No. 4,399,216. Such markers are proteins, generally enzymes, that enable the identification of transformant cells, i.e., cells which are competent to take up exogenous DNA. Generally, identification is by survival of transformants in culture medium that is toxic, or from which the cells cannot obtain critical nutrition without having taken up the marker protein.

Host cells such as insect cells (e.g., cultured *Spodoptera frugiperda* cells) and expression vectors such as the baculovirus expression vector (e.g., vectors derived from *Autographa californica* MNPV, *Trichoplusia ni* MNPV, Rachiplusia ou MNPV, or Galleria ou MNPV) may be employed in carrying out the present invention, as described in U.S. Pat. Nos. 4,745,051 and 4,879,236 to Smith et al. In general, a baculovirus expression vector comprises a baculovirus genome containing the gene to be expressed inserted into the polyhedrin gene at a position ranging from the polyhedrin transcriptional start signal to the ATG start site and under the transcriptional control of a baculovirus polyhedrin promoter.

The chimeric proteins described herein may be prepared per se or in the form of pharmaceutically acceptable salts thereof. For example, acid addition salts of acetate, adipate, alginate, aspartate, benzoate, benzenesulfonate, bisulfate, butyrate, citrate, camphorate, camphorsulfonate, cyclopentanepropionate, digluconate, dodecylsulfonate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylproprionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth.

Pharmaceutical formulations of the instant invention comprise the chimeric protein in a pharmaceutically acceptable carrier, such as sterile, pyrogen-free water or sterile pyrogen-free phosphate-buffered saline solution. The chimeric protein is included in an effective coagulation-promoting amount. The precise amount to be administered to the patient (i.e., a human patient) is determined in a routine manner, and will vary depending on the condition of the subject, route of administration (e.g., intravenous, subcutaneous, intraperitoneal). In general, for factor VIII, the dosage will range from 5 or 10 to 50, 500 or even 5,000 Units or more per kilogram subject body weight. Dosages for factor V may be the same, although in practice factor V dosage is typically determined by simply administering a factor V-containing preparation and monitoring the patient for the desired effect.

Diagnostic tests of the present invention may be carried out in accordance with known techniques. Such techniques provide a method of detecting antibody inhibitors to a blood coagulation protein in a patient (typically a human patient), comprising collecting an antibody-containing biological fluid sample (e.g., blood, blood plasma, or blood serum) from the patient; contacting the biological fluid sample to a chimeric blood coagulation protein as given herein; and then detecting the formation of a reaction product between said chimeric blood coagulation protein and antibodies in said biological fluid. Any suitable assay format, such as radioimmunoassay (RIA) or enzyme-linked immunosorbent assay (ELISA) may be employed, in accordance with known techniques. See, e.g., Immunology: Basic Processes, 162–175 (J. Bellanti Ed. 2d Ed. 1985)(W. B. Saunders Co.). To carry out epitope mapping, the assay is repeated with a biological sample from a single subject a plurality of times (or repetitions) with different chimeric proteins (e.g., a library of chimeric proteins) with each member of the library containing a different, predetermined, epitope (e.g., a different Factor VIII epitope in Factor V for Factor VIII epitope mapping; a different Factor V epitope in a Factor VIII for factor V epitope mapping). Identification of the particular chimera or chimeras with which patient antibodies react enables identification of the epitopes in those chimeras to which the alloantibody or autoantibody inhibitors in the patient are directed.

The present invention is explained in greater detail in the following Examples. These examples are for illustrative purposes only, and are not to be taken as limiting of the invention.

EXAMPLES

Construction of Light Chain Chimeras The full-length factor V cDNA in the plasmid pUC 18 and the full-length factor VIII cDNA in the plasmid pCNHS were used for the construction of all mutants. To prepare chimeras that precisely switched exon-size segments of factor VIII cDNA for the corresponding segment of factor V, a combination of restriction fragments and the polymerase chain reaction (PCR) were used, as previously described (ortel, TL, Devore-Carter, D, Quinn-Allen, MA, and Kane, WH. (1992) "Deletion Analysis of Recombinant Human Factor V. Evidence for a Phosphatidylserine Binding Site in the Second C-Type Domain" J. Biol them, 267: 4189–4198). The mutant $rHFV_{V,e25;VIII,e26}$, which has exon 26 of factor VIII substituted for exon 25 of factor V, was constructed as follows. The last exon of factor VIII was amplified using oligonucleotides 1 and 2 (Table 1). This fragment was restricted with Nco 1/Sal 1, and inserted with a Bam Hl/Nco 1 fragment from factor V (spanning residues 6000 through 6591 of the cDNA) into Bam Hl/sal 1 restricted pUC 18. A Bgl ll/Sal 1 fragment, spanning the entire chimeric C2 domain construct, was excised and subsequently ligated into the shuttle vector pCNVSS rHFV LC that had been restricted with Bgl ll/Sal 1. The resultant construct, containing the single exon switch, was restricted with Sph l/Sal 1, which released the entire chimeric light chain constructed from pCNVSS. This chimera was then ligated into pCNHS rHFV that had been cut with Sph l/Sal 1, replacing the light chain of factor V with the chimeric light chain.

The mutant $rHFV_{V,e24,25;VIII,e25,26}$, which has exons 25 and 26 of factor VIII substituted for exons 24 and 25 of factor V, was constructed using the PCR to splice exon 23 of factor V to exon 25 of factor VIII by overlap extension (SOE) (Ho, SN, Hunt, HD, Horton, RM, Pullen, JK, and Pease, IR. (1989) Gene, 77: 51). The PCR was used to amplify two segments of DNA, one spanning exons 19 through 23 of factor V and one spanning exons 25 and 26 of factor VIII, using oligonucleotides 3 and 4, and 5 and 6, respectively, as primers. The resultant PCR products overlapped by approximately 30 bp at the 3' end of exon 23 of factor V and the 5' end of exon 25 of factor VIII. These fragments were purified by agarose gel electrophoresis and used as the templates in a second PCR, using oligonucleotides 3 and 67 as primers. The resultant PCR fragment, spanning approximately 1000 bp, was restricted with Bam Hl/Sal 1 and shuttled into pCNVSS rHFV LC and the pCNHS rHFV, as described for $rHFV_{v,e25;VIII,e26}$.

The mutant $rHFV_{V,C2;VIII,C2}$, which contains the entire C2 domain of factor VIII substituted for the C2 domain of factor V, was constructed by using the PCR with factor V as a template and oligonucleotides 7 and 8 as primers. This resulted in an amplified C1 domain of factor V that possessed the first fifteen bases of the C2 domain of factor VIII, including an Sph 1 site. This fragment was restricted with Bam Hl /Sph 1 and was ligated with an Sph l/Sal 1 fragment from factor VIII (spanning the C2 domain) into Bam Hl/Sal 1 restricted pUC 18. The fragment was then excised with Bgl ll/Sal 1 and inserted into pCNVSS rHFV LC, as described for $rHFV_{V,e25;VIII,e26}$. Because of the Sph 1 site in exon 24 of factor VIII, this chimeric light chain was restricted with Nco l/Sal 1 and inserted into Nco l/Sal 1 restricted pCNHS rHFV.

The structures of all factor V chimeras were confirmed by extensive restricting mapping and DNA sequencing of all segments obtained by the PCR. The cDNA inserts were then excised from the plasmid by Cla l/Sal 1 and ligated into the expression vector $pDX_{ECSE}$. The resultant expression vectors were obtained from JM109 cells using the alkaline lysis method, as previously described (Ortel, supra).

Transient Expression of Factor V Chimeras in COS cells COS-7 cells were transfected with the individual mutant plasmid constructs by calcium phosphate precipitation as described previously (Ortel, supra).

TABLE 1

| Mutant | Oligonucleotide | Strand | Sequence | SEQ ID NO |
|---|---|---|---|---|
| $rHFV_{V,e25; VIII,e26}$ | 1 | + | TCCTCCATGGTGGACAAGGTTTTTCAGGGAAATCAAG | SEQ ID NO:1 |
| | 2 | − | CACAGTCGACTCAGTAGAGGTCCTGTGCCTC | SEQ ID NO:2 |
| $rHFV_{V,e24-25; VIII,e25,25}$ | 3 | + | AATGCCTGGCAAGCCAAGGTGAATAATCCAAAAGAG | SEQ ID NO:3 |
| | 4 | − | CACAGTCGACTCAGTAGAGGTCCTGTGCCTC | SEQ ID NO:4 |
| | 5 | + | CACAGGTACCTCAGAGACTGTAGGATGCCA | SEQ ID NO:5 |
| | 6 | − | CTCTTTTGGATTATTCACCTTGGCTTGCCAGGCATT | SEQ ID NO:6 |
| $rHRV_{V,C2; VIII,C2}$ | 7 | + | CACAGGTACCTCAGAGACTGTAGGATGCCA | SEQ ID NO:7 |
| | 8 | − | CAATGGCATGCTGCAACTATTTACCTCACAACCTTG | SEQ ID NO:8 |

The foregoing examples are illustrative of the present invention, and are not to be construed as limiting thereof. The invention is defined by the following claims, with equivalents of the claims to be included therein.

What is claimed is:

1. A chimeric blood coagulation protein selected from the group consisting of:
    coagulation factor V comprising a light chain in which from one to five A3 domain exons are replaced with the homologous exons of coagulation factor VIII; and
    coagulation factor VIII comprising a light chain in which from one to five A3 domain exons are replaced with the homologous exons of coagulation factor V.

2. A chimeric blood coagulation protein selected from the group consisting of:

coagulation factor V in which from one to two factor V light chain exons are replaced with the homologous exons of coagulation factor VIII; and coagulation factor VIII in which from one to two factor VIII light chain exons are replaced with the homologous exons of coagulation factor V.

3. A chimeric blood coagulation protein selected from the group consisting of:

coagulation factor V comprising a light chain in which a plurality of exons thereof are replaced with the homologous exons of coagulation factor VIII, subject to the proviso that fewer than all exons are exchanged in any domain of the light chain; and coagulation factor VIII comprising a light chain in which a plurality of exons thereof are replaced with the homologous exons of coagulation factor V, subject to the proviso that fewer than all exons are exchanged in any domain of the light chain.

4. A chimeric blood coagulation protein selected from the group consisting of:

coagulation factor V comprising a light chain in which from one to three C1 domain exons are replaced with the homologous exons of coagulation factor VIII; and coagulation factor VIII comprising a light chain in which from one to three C1 domain exons are replaced with the homologous exons of coagulation factor V.

5. A chimeric blood coagulation protein selected from the group consisting of:

coagulation factor V in which from one to two C2 domain exons are replaced with the homologous C2 domain exons of coagulation factor VIII; and coagulation factor VIII in which from one to two C2 domain exons are replaced with the homologous C2 domain exons of coagulation factor V.

6. An isolated DNA encoding a chimeric blood coagulation protein according to claim 1.

7. A vector comprising isolated DNA according to claim 6.

8. An isolated DNA molecule encoding a chimeric blood coagulation protein according to claim 1, claim 4, claim 5, claim 16 or claim 17.

9. A eukaryotic host cell containing a vector according to claim 7 and capable of expressing said DNA.

10. A chimeric blood coagulation protein selected from the group consisting of:

Factor VIII$_{(VIII-15;V-14)}$;
Factor VIII$_{(VIII-16;V-15)}$;
Factor VIII$_{(VIII-17;V-16)}$;
Factor VIII$_{(VIII-18;V-17)}$;
Factor VIII$_{(VIII-19;V-18)}$;
Factor VIII$_{(VIII-20;V-19)}$;
Factor VIII$_{(VIII-21;V-20)}$;
Factor VIII$_{(VIII-22;V-21)}$;
Factor VIII$_{(VIII-23;V-22)}$;
Factor VIII$_{(VIII-24;V-23)}$;
Factor VIII$_{(VIII-25;V-24)}$;
Factor VIII$_{(VIII-26;V-25)}$;
Factor V$_{(V-14;VIII-15)}$;
Factor V$_{(V-15;VIII-16)}$;
Factor V$_{(V-16;VIII-17)}$;
Factor V$_{(V-17;VIII-18)}$;
Factor V$_{(V-18;VIII-19)}$;
Factor V$_{(V-19;VIII-20)}$;
Factor V$_{(V-20;VIII-21)}$;
Factor V$_{(V-21;VIII-22)}$;
Factor V$_{(V-22;VIII-23)}$;
Factor V$_{(V-23;VIII-24)}$;
Factor V$_{(V-24;VIII-25)}$;
Factor V$_{(V-25;VIII-26)}$;
Factor VIII$_{(VIII-15,16;V-14,15)}$;
Factor VIII$_{(VIII-16,17;V-15,16)}$;
Factor VIII$_{(VIII-17,18;V-16,17)}$;
Factor V$_{(V-14,15;VIII-15,16)}$;
Factor V$_{(V-15,16;VIII-16,17)}$;
Factor V$_{(V-16,17;VIII-17,18)}$;
Factor VIII$_{(VIII-20,21;V-19,20)}$;
Factor VIII$_{(VIII-21,22;V-20,21)}$;
Factor VIII$_{(VIII-22,23;V-21,22)}$;
Factor VIII$_{(VIII-23,24;V-22,23)}$;
Factor VIII$_{(VIII-24,25;V-23,24)}$;
Factor VIII$_{(VIII-25,26;V-24,25)}$;
Factor V$_{(V-19,20;VIII-20,21)}$;
Factor V$_{(V-20,21;VIII-21,22)}$;
Factor V$_{(V-21,22;VIII-22,23)}$;
Factor V$_{(V-22,23;VIII-23,24)}$;
Factor V$_{(V-23,24;VIII-24,25)}$;
Factor V$_{(V-24,25;VIII-25,26)}$; and
Factor VIII$_{(VIII-20,21,22;V-19,20,21)}$.

11. A chimeric blood coagulation protein selected from the group consisting of:

Factor VIII$_{(VIII-20;V-19)}$;
Factor VIII$_{(VIII-21;V-20)}$;
Factor VIII$_{(VIII-22;V-21)}$;
Factor VIII$_{(VIII-23;V-22)}$;
Factor VIII$_{(VIII-24;V-23)}$;
Factor VIII$_{(VIII-25;V-24)}$;
Factor VIII$_{(VIII-26;V-25)}$;
Factor V$_{(V-19;VIII-20)}$;
Factor V$_{(V-20;VIII-21)}$;
Factor V$_{(V-21;VIII-22)}$;
Factor V$_{(V-22;VIII-23)}$;
Factor V$_{(V-23;VIII-24)}$;
Factor V$_{(V-24;VIII-25)}$;
Factor V$_{(V-25;VIII-26)}$;
Factor VIII$_{(VIII-20,21;V-19,20)}$;
Factor VIII$_{(VIII-21,22;V-20,21)}$;
Factor VIII$_{(VIII-22,23;V-21,22)}$;
Factor VIII$_{(VIII-23,24;V-22,23)}$;
Factor VIII$_{(VIII-24,25;V-23,24)}$;
Factor VIII$_{(VIII-25,26;V-24,25)}$;
Factor V$_{(V-19,20;VIII-20,21)}$;
Factor V$_{(V-20,21;VIII-21,22)}$;
Factor V$_{(V-21,22;VIII-22,23)}$;
Factor V$_{(V-22,23;VIII-23,24)}$;
Factor V$_{(V-23,24;VIII-24,25)}$; and
Factor V$_{(V-24,25;VIII-25,26)}$.

12. An isolated DNA molecule encoding a chimeric blood coagulation protein according to any of claims 10 or 11.

13. A vector comprising isolated DNA according to claim 12.

14. A eukaryotic host cell containing a vector according to claim 13.

15. A eukaryotic host cell containing a vector according to claim 13 and capable of expressing said DNA.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
( A ) LENGTH: 37 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:1:

TCCTCCATGG TGGACAAGGT TTTTCAGGGA AATCAAG 37

( 2 ) INFORMATION FOR SEQ ID NO:2:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:2:

CACAGTCGAC TCAGTAGAGG TCCTGTGCCT C 31

( 2 ) INFORMATION FOR SEQ ID NO:3:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:3:

AATGCCTGGC AAGCCAAGGT GAATAATCCA AAAGAG 36

( 2 ) INFORMATION FOR SEQ ID NO:4:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:4:

CACAGTCGAC TCAGTAGAGG TCCTGTGCCT C 31

( 2 ) INFORMATION FOR SEQ ID NO:5:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:5:

CACAGGTACC TCAGAGACTG TAGGATGCCA                                          30

( 2 ) INFORMATION FOR SEQ ID NO:6:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

CTCTTTTGGA TTATTCACCT TGGCTTGCCA GGCATT                                   36

( 2 ) INFORMATION FOR SEQ ID NO:7:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

CACAGGTACC TCAGAGACTG TAGGATGCCA                                          30

( 2 ) INFORMATION FOR SEQ ID NO:8:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

CAATGGCATG CTGCAACTAT TTACCTCACA ACCTTG                                   36